US008503741B2

(12) United States Patent
Redel

(10) Patent No.: US 8,503,741 B2
(45) Date of Patent: Aug. 6, 2013

(54) WORKFLOW OF A SERVICE PROVIDER BASED CFD BUSINESS MODEL FOR THE RISK ASSESSMENT OF ANEURYSM AND RESPECTIVE CLINICAL INTERFACE

(75) Inventor: Thomas Redel, Poxdorf (DE)

(73) Assignee: Siemens Aktiengesellschaft, München (DE)

( * ) Notice: Subject to any disclaimer, the term of this patent is extended or adjusted under 35 U.S.C. 154(b) by 1219 days.

(21) Appl. No.: 11/607,569

(22) Filed: Nov. 30, 2006

(65) Prior Publication Data

US 2008/0132781 A1 Jun. 5, 2008

(51) Int. Cl.
*G06K 9/00* (2006.01)
(52) U.S. Cl.
USPC ............................................ 382/128; 345/424
(58) Field of Classification Search
USPC ............................................ 382/128; 703/11
See application file for complete search history.

(56) References Cited

U.S. PATENT DOCUMENTS

| 6,047,080 | A * | 4/2000 | Chen et al. .................... | 382/128 |
| 6,708,141 | B1 * | 3/2004 | Schaff et al. ....................... | 703/2 |
| 2001/0017937 | A1 * | 8/2001 | Bonnefous ................... | 382/128 |
| 2002/0002447 | A1 * | 1/2002 | Keane ............................ | 703/11 |
| 2002/0136440 | A1 * | 9/2002 | Yim et al. ...................... | 382/131 |
| 2003/0234781 | A1 * | 12/2003 | Laidlaw et al. ................. | 345/419 |
| 2005/0002547 | A1 * | 1/2005 | Torre-Bueno .................. | 382/128 |
| 2005/0259854 | A1 * | 11/2005 | Arimura et al. ................ | 382/130 |
| 2006/0013462 | A1 * | 1/2006 | Sadikali ........................ | 382/132 |

OTHER PUBLICATIONS

Charles A. Taylor, Thomas J. R. Hughes, Christopher K. Zarins, Finite element modeling of blood flow in arteries, Computer Methods in Applied Mechanics and Engineering, vol. 158, Issues 1-2, May 25, 1998, pp. 155-196, ISSN 0045-7825, DOI: 10.1016/50045-7825(98)80008-X.*
Tamer Hassan et al.; Computational Replicas: Anatomic Reconstructions of Cerebral Vessels as Volume Numerical Grids at Three-Dimensional Angiography; Sep. 2004; AJNR Am J Neuroradiol 25:1356-1365, American Society of Neuroradiology.
John F. LaDisa, Jr. et al.; Stent design properties and deployment ratio influence indexes of wall shear stress: a three-dimensional computational fluid dynamics investigation within a normal artery; Jul. 2004 (first published Feb. 6, 2004). Journal of Applied Physiology 97:424-430.

(Continued)

*Primary Examiner* — Hadi Akhavannik
(74) *Attorney, Agent, or Firm* — Lempia Summerfield Katz LLC

(57) ABSTRACT

A system and method provide an optimized workflow and a dedicated user interface for image visualizations that facilitate medical diagnosis. Image data may be acquired via an imaging procedure at a remote medical facility. A physician may review the images on a display and mark-up/modify the images via the interface to create user-defined data. The image and user-defined data may be transmitted to a service provider. At the service provider, a software technician may generate a medical simulation using the image and user-defined data. The medical simulation may simulate actual conditions within the patient. Subsequently, the simulation results may be transferred to, or otherwise remotely accessed via a network from, the remote medical facility. As a result, medical treatment provided by remote facilities, which may only have limited resources in terms of personnel and equipment, may be enhanced and inefficiencies associated with the generation of medical simulations may be alleviated.

29 Claims, 4 Drawing Sheets

OTHER PUBLICATIONS

Juan R. Cebral et al.; Cerebral Aneursym Hemodynamics Modeling From 3D Rotational Angiography; ©2004 IEEE Symposium on Biomedical Imaging (ISBI 2004), pp. 944-947; School of Computational Sciences, George Mason University Interventional Radiology, Inova Fairfax Hospital.

Kamen N. Beronov et al.; Progress towards simulation-based medical planning of intracranial aneurysm treatment, based on lattice Boltzmann DNS (1 page); Inst. for Fluid Mechanics, Univ. Erlangen-Nuernberg.

Syngo MultiModality Applications Brochure; © Nov. 2005 Siemens AG; pp. 1-17; Siemens Medical.

* cited by examiner

WORKFLOW OF A SERVICE PROVIDER BASED CFD BUSINESS MODEL FOR THE RISK ASSESSMENT OF ANEURYSM AND RESPECTIVE CLINICAL INTERFACE

BACKGROUND

The present embodiments relate generally to interactive software applications that assist a user. More particularly, the present embodiments relate to interactive software applications that perform operations on medical image data.

Conventional systems may perform operations on datasets to reproduce images to facilitate medical diagnosis. The images may be visualized on a display using various methods. Known volume visualization methods include multi-planar reconstruction, maximum intensity projection, volume rendering, and surface shading. In the case of vessels being displayed, a multi-planar reformatted image perpendicular to each actual vessel position may be generated. Virtual flight, i.e. movement, through hollow vessels may be simulated.

However, conventional techniques of generating such image visualizations may be cumbersome and inefficient. Typically, simulations and visualizations may only be adequately produced by interdisciplinary personnel, such as physicians and software technicians, interactively working together. Initially, a physician may perform an imaging procedure to acquire image data. After which, conventional simulations may be developed using a plurality of different hardware/software tools. The different tools may impose unwanted restrictions upon simulation generation and require a fixed degree of cooperation between physician and technician. Additionally, local medical facilities may only have limited resources, hindering development of complex simulations. Finally, any medical interpretation based on a simulation may be handicapped by the underlying simulation, the quality of simulation being dependent upon the degree of expertise of those who develop it.

BRIEF SUMMARY

By way of introduction, the embodiments described below include methods, processes, apparatuses, instructions, or systems for an optimized workflow and a dedicated user interface that provide image visualizations to facilitate medical diagnosis. The workflow and interface may each be used to generate a medical simulation. For instance, the medical simulation may simulate blood flow inside of a vessel, organ, or other anatomical structure. The workflow may involve (1) acquiring internal image data of a patient at a remote medical facility, (2) displaying, via a dedicated user interface, a segmented geometry specific to the patient using the image data, (3) accepting user operations, via the dedicated interface, that modify the segmented geometry, (4) transferring the image data, as well as additional patient specific data, to a central location associated with a service provider, (5) simulating blood flow within the modified segmented geometry and interpreting the simulation results at the central location, (6) transferring the simulation and/or the interpretation results to the remote medical facility, and/or (7) running the simulation at the remote medical facility. The dedicated user interface may assist the user in properly modifying or otherwise prepping the segmented geometry and adding additional input for simulation generation.

As a result, medical simulations may be generated at a central location associated with a service provider having more available resources in terms of skilled medical/software personnel and equipment than a remote medical facility. The medical simulations may then be transferred to and/or remotely accessed by personnel at the remote facility. Accordingly, the workflow and dedicated interface may enhance the quality of medical simulations generated and any subsequent interpretation thereof. The workflow and dedicated interface may alleviate inefficiencies associated with conventional techniques of simulation generation. In one embodiment, a Computational Fluid Dynamics (CFD) or other algorithm is used to simulate blood flow within cerebral blood vessels to facilitate analysis of the projected initiation, growth, and possible rupture of aneurysms.

In a first aspect, a method provides image visualization for medical diagnosis. The method includes receiving image data associated with a patient from a remote location via a communications network at a central location, generating a medical simulation tailored to the patient based upon the image data received at the central location, and transmitting simulation data by which to reproduce the medical simulation from the central location to the remote location via the communications network or otherwise providing remote access to the medical simulation via the communications network.

In a second aspect, a method provides image visualization for medical diagnosis. The method includes receiving data associated with a patient from a remote location via a network at a central location, and generating a medical simulation at the central location, the medical simulation visually simulates blood flow within the patient based upon the data received. The method also includes transmitting resultant data by which to reproduce the medical simulation from the central location to the remote location via the network or otherwise providing remote access to the medical simulation via the network.

In a third aspect, a data processing system provides image visualization that facilitates medical diagnosis. The system may include a memory unit operable to store image data associated with internal images of a patient, a processing unit operable to access the image data stored and display a segmented geometry of an anatomical structure shown in the internal images on a display, and a user interface operable to accept a user-selected parameter associated with a modification of the segmented geometry to generate user-defined data. The user-defined data is stored in the memory unit such that the modified segmented geometry may be subsequently reconstructed using the user-defined data.

In a fourth aspect, a computer-readable medium having instructions executable on a computer is described. The instructions include receiving image data associated with internal images of a patient, displaying a segmented geometry of an anatomical structure shown within the internal images, accepting a user-selected operation that modifies the segmented geometry, and generating user-defined data that correlates the user-selected operation with the segmented geometry such that the segmented geometry as modified may be subsequently reconstructed.

The present invention is defined by the following claims. Nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The present embodiments will become more fully understood from the detailed description given herein below and the accompanying drawings which are given by way of illustration only, and are not limitative of the present invention, and wherein.

DETAILED DESCRIPTION OF THE DRAWINGS AND PRESENTLY PREFERRED EMBODIMENTS

Figure 1:
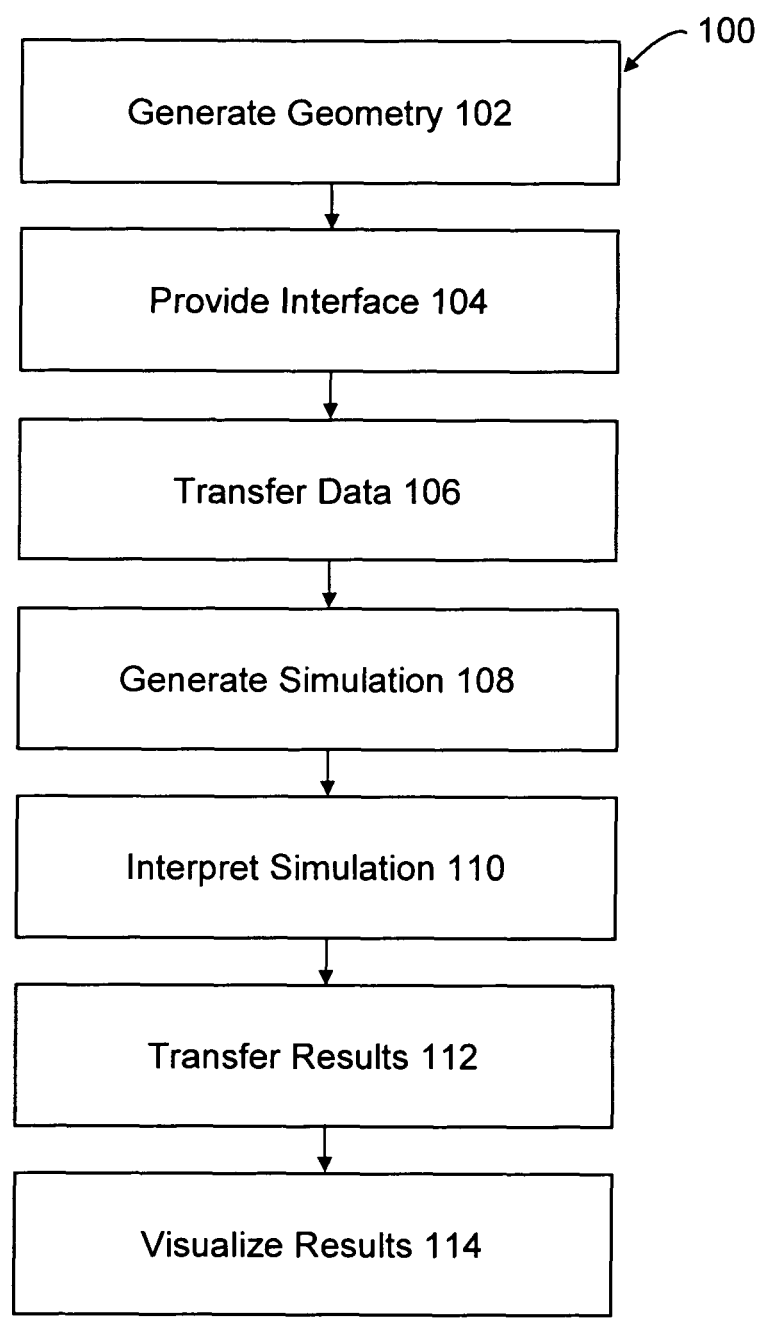
FIG. 1 illustrates an exemplary method of image visualization for medical diagnosis.

The embodiments described herein include methods, processes, apparatuses, instructions, or systems for an optimized workflow and a dedicated user interface that provide image visualization to facilitate medical diagnosis. The workflow may involve acquiring internal image data of a patient at a remote medical facility using an imaging procedure. The image data may be viewed via a dedicated user interface on a display at the remote facility. The images displayed may include a segmented geometry of an anatomical structure specific to the patient.

Medical personnel at the remote facility may determine various user-selected parameters, including simulation-related recommendations, to enhance the accuracy of a medical simulation to be generated at a service provider based upon the image data. The recommendations may include a suggested modification of a segmented geometry, defining a vessel inlet or outlet, suggesting a region of interest or artifact to analyze via the simulation, and/or other recommendations. The recommendations may be recorded as or converted into data to be transferred to the service provider for use during the generation of the simulation.

For instance, a physician or other remote medical facility personnel may determine that the segmented geometry displayed should be modified to enhance the accuracy of the medical simulation. Accordingly, user-selected parameters/ recommendations or operations may be accepted, via the dedicated user interface, that modify or otherwise "mark-up" the segmented geometry. The dedicated interface may provide guidance to the user while the image data is being modified. User-defined data corresponding to the user-selected parameters/operations and/or correlating user-selected parameters/operations with a particular segmented geometry may be generated and stored. The segmented geometry as modified may be subsequently reconstructed using the image and user-defined data.

The image data, as well as the user-defined data defining various modifications to the images shown in the image data, may be transferred to a service provider or other central location via a communications network. At the service provider, software technicians or other specialists may generate software that simulates blood flow within a patient specific geometry, such as a patient specific geometry as previously modified at the remote facility. A medical interpretation of the simulation results also may be performed by the service provider.

The simulation results and/or interpretation thereof may be transferred from the service provider to the remote medical facility via the communications network or otherwise remotely accessed from the remote facility via the network.

The simulation may be run on local computers at the remote facility. As a result, medical simulations may be generated at a service provider having more available resources in terms of skilled personnel and equipment than remote facilities. Accordingly, the workflow and dedicated interface may enhance the quality of medical simulations, as well as any corresponding interpretations of the underlying simulations.

I. Conventional Workflows

A conventional workflow may involve steps related to (1) the generation of patient specific geometry, (2) simulation, and (3) interpretation. With conventional techniques, appropriate geometry generation may require that a physician use his or her personal experience in image generation and interpretation. However, in such a case, suboptimal results may be generated further requiring that the physician perform additional imaging procedures or combine different images to achieve satisfactory geometry, satisfactory geometry generation being a prerequisite to high quality simulation results. Additionally, conventional techniques may require interaction between physicians and software technicians at each major step in the process. Hence, conventional techniques may be cumbersome, time-consuming, and inefficient. Moreover, typically simulations may not be generated at remote medical facilities due to limited resources.

II. Optimized Workflow and Dedicated Interface

Accordingly, the embodiments described herein provide an optimized workflow and a defined interface that transfer information among interdisciplinary experts at the completion of various steps during simulation generation and interpretation. The workflow and interface may provide for a more efficient completion of the overall simulation process. Additionally, the simulation results may be accessed from remote medical facilities having only a limited number of patients and/or resources, such that enhanced quality medical treatment is provided.

The medical simulation may simulate the blood flow inside of an anatomical structure, such as a vessel, organ, or other bodily structure, represented by image data of structure within a patient. For instance, the blood flow within an individual vessel geometry tailored to a specific patient may be simulated to facilitate medical diagnosis. In one embodiment, the generation of the patient specific geometry may include the imaging of a diseased vessel segment by various methods. The image dataset acquired may be reconstructed and segmented for the generation of a surface representation of the vessel or a vessel segment.

The simulation of blood flow may be used to detect and analyze the onset and growth of atherosclerotic disease or other medical conditions, as well as for the development and simulation of new medical devices. For instance, the initiation, growth, and/or rupture of vascular aneurysms may be correlated to the local blood flow inside of a vessel and/or to the interaction between the local blood flow and the vessel wall.

Computational Fluid Dynamics (CFD) or other algorithms may be employed to generate the simulation. The simulation may be based upon various geometric models, such as magnetic resonance imaging (MRI), computed tomography (CT), x-ray, three-dimensional rotational angiography, three-dimensional intravascular ultrasound, positron emission tomography (PET), or other models.

Within the workflow, the generation of the simulation may involve several sub-steps, such as the "mark-up" of the geometry, the generation of a volume grid or other mesh, and the production of the simulation itself. The mark-up of the geometry may involve the determination of various user-selected parameters, such as blood flow, shear stress, and/or local pressure. The user-selected parameters may be selected by a physician, extracted from image data, or otherwise determined.

For instance, a physician or other medical personnel may perform internal imaging using various procedures. A dedicated user interface may then be employed to define an appropriate segmentation of the patient's individual vessel geometry upon which to base a simulation. The interface may permit the physician to select various boundary conditions, such as inflow, blood parameters, inlets, outlets, and other user-selected parameters/recommendations. The interface may permit the physician to make other modifications associated with the image data. User-defined data associated with the user-selected parameters/recommendations and other modifications to the image data accepted by the interface may be generated and stored in a memory unit such that the mark-up of the images may be subsequently reconstructed.

The interface may provide guidance to the user regarding the proper modification of displayed images. The assistance may be provided in textual, graphical, audible, or other formats. The assistance may provide medical information, information related to the operation of the interface, information related to image modification or simulation generation, and/or other information.

The interface may permit the user to enter and store text messages related to certain images to facilitate simulation generation. For instance, a physician may want to pass along specific information, such as simulation-related recommendations, to a software technician who will create the simulation. The interface may allow communication between physician and technician regarding various images, image geometries, and modifications thereto.

After the physician has marked up the data via the dedicated interface, the image data and user-defined data associated with the user-selected parameters/recommendations may be transferred to a service provider. The service provider may employ the same dedicated interface as the remote medical facility to facilitate reconstruction of the mark-up of the patient's geometry. For example, a software technician at the service provider may use the same interface to view any user-selected parameters selected, or operations performed upon the image data, at the remote facility, as well as any text messages provided. The software technician may generate an optimized surface representation, a volume grid or other mesh, and the simulation itself using the image data and the user-defined data received. Hence, unlike conventional techniques that may require a plurality of different programs and direct interaction between physician and technician, the dedicated interface may operate on machines at both the remote facility and the location of the service provider.

III. Exemplary Workflow and Interfaces

FIG. 1 illustrates an exemplary method of image visualization for medical diagnosis 100. The workflow 100 may include generating a patient specific geometry 102 at a remote medical facility, providing a dedicated user interface 104, transferring image and user-defined data 106 to a service provider, generating a simulation 108 at the service provider, interpreting the simulation 110, transmitting or providing remote access to the results 112, and/or visualizing the results 114 at the remote facility. The workflow may include additional, fewer, or alternative steps.

The workflow 100 may include the generation of an image of an anatomical structure within a patient 102. For example, a multi-dimensional image of a diseased vessel, organ, or other anatomical structure may be generated. Internal images of a patient may be acquired during a pre-interventional procedure, such as a MRI, CT, PET, x-ray, angiography, or other procedure. Alternatively, the internal images may be acquired during an intervention, such as with a camera or other imaging device during surgery, or via a catheter, needle, or other medical device equipped with a camera that is inserted into a patient. The images acquired may be displayed at various angles/geometries using known techniques that provide for rotation of and/or flight through images.

The workflow 100 may include generating a "mark-up" or other customization of the image data prior to simulation generation via a dedicated user interface 104. For example, the mark-up may be performed in a special interface module or other dedicated interface. In one embodiment, the interface is a software application that operates in conjunction with Syngo™ software. Other software applications may be used.

The dedicated interface may have access to image data, as well as a database associated with a medical facility and/or an interconnected network of hospitals. The interface may be used to perform several sub-steps associated with the workflow. Each sub-step may be represented by an individual task card, pop-up menu, icon, plug-in, or other interactive control element. Each sub-step may have an associated online guide available via a communications network or a memory unit. The online guide may provide graphical, textual, audible, or other guidance associated with the performance of the sub-steps.

Figure 2:
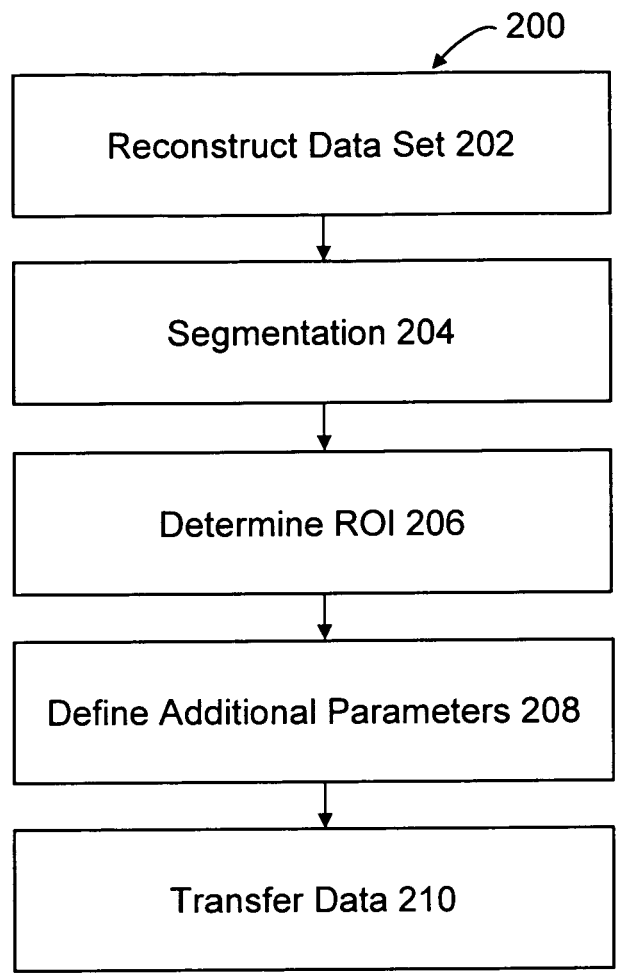
FIG. 2 illustrates an exemplary method of customizing image data for simulation generation.

As illustrated by FIG. 2, the dedicated user interface 200 may provide for reconstruction of an image dataset 202, segmentation of various geometries within image data 204, determining a region of interest 206, defining additional parameters to enhance the simulation 208, and transferring the image data and user-defined data generated to a service provider 210. The interface may provide additional, fewer, or alternative functions.

The dedicated interface may permit the reconstruction of an image or other dataset 202 used to generate the medical simulation. A defined set of reconstruction parameters may be predetermined that facilitate dataset reconstruction. The reconstruction parameters may be stored in a database or memory unit. The dedicated interface may allow the user to select a number of the reconstruction parameters as user-selected parameters. The user-selected parameters may be stored as user-defined data in a separate dataset.

In one embodiment, the datasets may be formatted in the DICOM (Digital Imaging and Communications in Medicine) standard. DICOM is a standard that permits different modalities to exchange data, such as patient data, examination requests, images, and other medical data. The standard permits interoperability between different medical device/service vendors. As such, the standard may facilitate remote data transfer between a remote medical facility and a service provider.

The interface may permit segmentation of an anatomical structure shown within the image data 204, such as a blood vessel. The segmentation of a patient geometry may be generated using any now known or later developed techniques, such as via a combination of well known threshold and region growing processes. The result may be represented as a surface grid or mesh, Point Cloud™, or other known multi-dimensional techniques.

The interface may permit the user to select or cut out a region of interest (ROI) for emphasis and to analyze 206. The enhanced region of interest may be associated with the brain, the abdomen, the heart, the liver, a lung, a breast, the head, a limb or any other body area. Images of the region of interest may illustrate an anatomical structure, such as a vessel, organ, or other hollow bodily structure. The region of interest may include one or more artifacts to be analyzed.

The interface may permit the user to define additional parameters 208 to enhance the quality of the simulation to be generated. For instance, the interface may permit the user to modify a segmentation of the patient's geometry. The user, such as a physician, may modify the segmented geometry or the surface representation. The user may identify and mark artifacts for analysis, as well as add specific text notes for the service provider as to how to remove and/or repair the representation of the artifacts shown in the image data.

The interface may permit the user to identify and define an inlet and/or outlet of an anatomical structure. In one embodiment, the interface or an associated processor may provide an automated option that automatically detects the inlet and outlet of vessels and other structures, such as using recognition algorithms upon image data. The structures automatically identified may be emphasized on the images displayed.

The interface may permit the user to define a dataset of inflow and/or pressure curves. The interface may permit the use of actual measurements of the inflow condition and/or patient adapted pressure curves. The interface may permit the user to select an appropriate inflow dataset from a group of time dependent inflow sets. The datasets may be characterized or stored in accordance with a medical characteristic, such as age, sex, disease, or other medical condition.

The interface may permit the user to select a particular viscosity of blood that should be accounted for by the simulation. The viscosity of a patient's blood may depend upon a state of a disease or the intake of certain drugs. Alternatively, a simulation may be dependent upon a specific medical device to be inserted into the patient. Hence, the interface may permit the user to select which device should be virtually placed within a blood vessel or other anatomical structure associated with the simulation.

The interface may permit the user to identify the importance of generating the simulation to the service provider. The interface may generate a user-selected priority mark associated with the patient. The priority corresponding to the priority mark may be high if the dataset is needed immediately. For instance, during an intervention the simulation may be needed in substantially real time to facilitate medical treatment during the intervention, as well as avoid a potential subsequent intervention procedure.

The workflow may transfer data via a network to a service provider 106. All relevant data required to generate a simulation may be transferred from the remote facility to an external service provider. The data may be related to (1) reconstructing the patient geometry in a surface representation using a standard template library, Point Cloud™ processing software, voxel modeling, or other software and include information defining inlets and outlets; (2) requested results, such as flow, shear stress, pressure, risk assessment, or other desired information; (3) boundary conditions such as inflow and pressure curves, or blood viscosity; (4) devices to be implanted and included in the simulation in accordance with their positioning within the anatomical structure; and (5) a patient specific identification flag that permits the remote medical facility to inform the service provider regarding long-term follow-up care of the patient. In a situation involving follow-up treatment, the service provider may provide a discount for any future services. Additionally, the data may be related to (6) a flag for priority, and (7) information associated with the proper billing by the services provider for services such as simulation generation and interpretation, which information may be automatically generated by the dedicated interface. The data may be transferred between the remote facility and the service provider in a secure mode.

The interface may permit the user to transmit image and mark-up data to a service provider via a send button 210. After which, the interface may automatically verify the completeness of the data to be transferred. In one embodiment, only if all of the requisite data has been defined, will a requested transfer of the data be completed via a network to a predefined address associated with a service provider. Otherwise, a warning may be generated informing the user of the missing information.

The workflow may include generating a medical simulation 108. At the location of the service provider, the simulation of the blood flow may be generated using known techniques, such as finite element based methods, Lattice Boltzman based methods, other algorithm based methods, or other techniques. The simulation may involve the generation of a volume grid or other mesh.

In one embodiment, the simulation may be performed on a computer having scalar and/or vector processors, such as a supercomputer or other high-performance machine. The computer may include a number of processors operating as a parallel processing system or other configuration. The capabilities of the computer may permit the simulation generated to simulate the elasticity of vessel walls and other effects typically neglected with current simulations. The simulation may permit analysis of flow, wall shear stress, temporal and spatial derivation from the local pressure, and/or other parameters.

The workflow may include interpreting the simulation results 110. The service provider may offer to perform an initial medical interpretation of the simulation results as an additional service. The service provider may have access to a number of simulations related to various patients. As a result, the service provider may organize a database that includes multiple simulations and corresponding image data and analysis. The database may be combined with a knowledge based system, such as a case-based reasoning system, neural network, or other system to provide expert analysis. The knowledge based system may interpret the simulation result, such as analyze the risk that a specific aneurysm will rupture. As time goes by and more simulations are generated, the database may be updated to further enhance provided analysis. In one embodiment, the system may be capable of searching a database based upon a patient characteristic to locate data, simulations, and previous diagnosis associated with a previous patient having similar characteristics.

The workflow may include transferring the simulation and/or interpretation results from the service provider to the remote medical facility 112. Resultant data associated with the simulation and interpretation results may be transferred to the remote facility or otherwise remotely accessed via a secure network from the remote facility. The resultant data may permit the remote facility to run the simulation. In one embodiment, the data may permit the reconstruction of a three-dimensional representation with temporal resolution. Other reconstructions may be provided for.

The visualization of the simulation result may be performed via volume rendering or other known techniques. For instance, the simulations may be generated using techniques described in Cebral et al. (*Cerebral Aneurysm Hemodynamics Modeling from 3D Rotational Angiography*), LaDisa et al. (*Stent Design Properties and Deployment Ratio Influence Indexes of Wall Shear Stress: A Three-Dimensional Computational Fluid Dynamics Investigation Within a Normal Artery*), and Hassan et al. (*Computational Replicas: Anatomic Reconstructions of Cerebral Vessels as Volume Numeri-*

*cal Grids at Three-Dimensional Angiography*), which are incorporated by reference herein in their entireties. Other techniques may be used.

IV. Exemplary Data Processor

Figure 3:
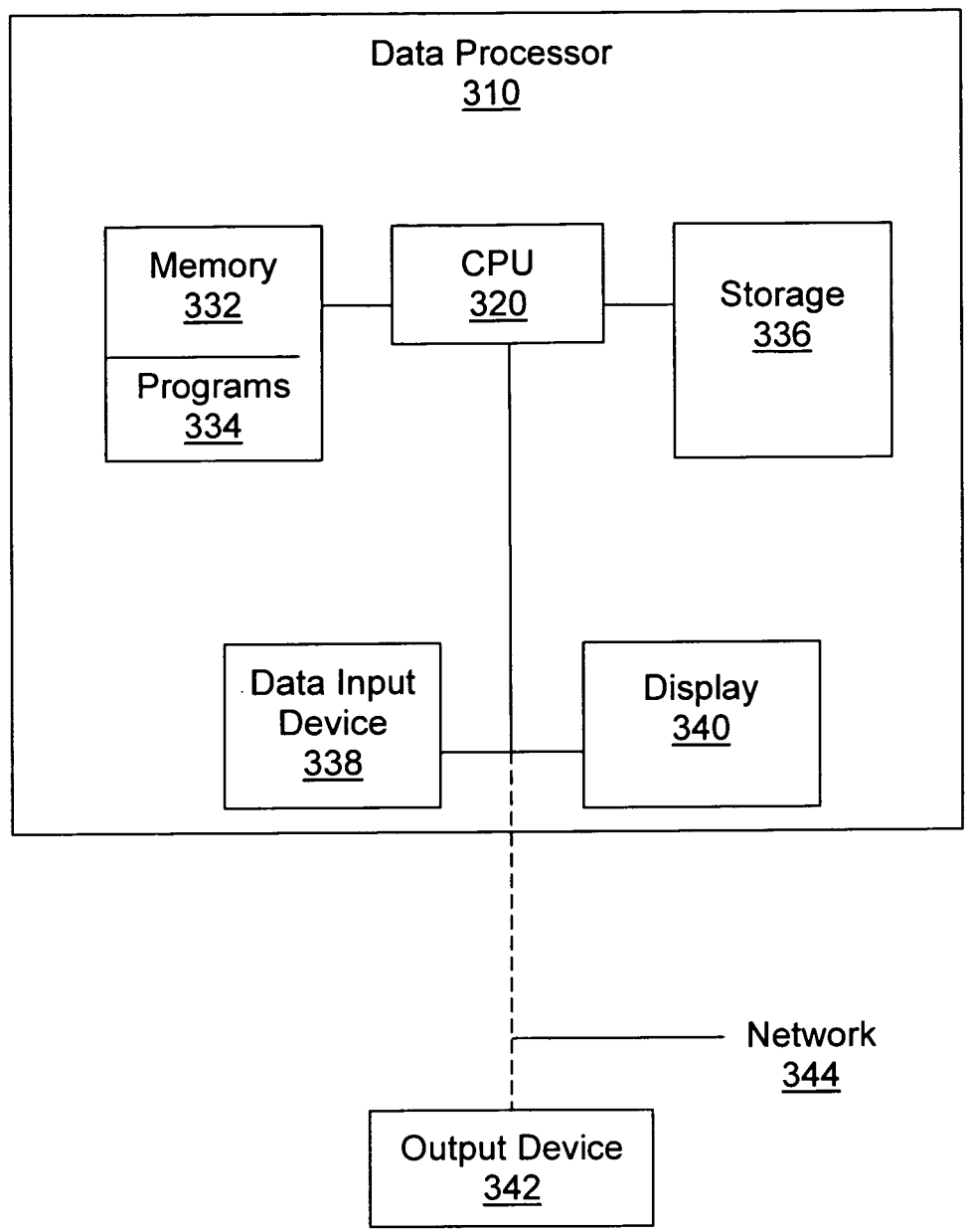
FIG. 3 illustrates an exemplary data processing system operable to provide image visualization for medical diagnosis.

The method of image visualization may be facilitated by a data processing system. FIG. 3 is a block diagram of an exemplary data processor 310 configured or adapted to provide functionality for image visualization. The data processor 310 may include a central processing unit (CPU) 320, a memory 332, a storage device 336, a data input device 338, and a display 340. The data processor 310 also may have an external output device 342, which may be a display, a monitor, a printer or a communications port. The data processor 310 may be a personal computer, work station, server, PACS station, medical imaging system, or other system. The data processor 310 may be interconnected to a network 344, such as an intranet, the Internet, or an intranet connected to the Internet. The data processor 310 may be interconnected to another location via the network 344 either by data lines or by wireless communication. The data processor 310 is provided for descriptive purposes and is not intended to limit the scope of the present system. The data processor may have additional, fewer, or alternate components.

A program 334 may reside on the memory 332, storage device 336, or another memory (e.g., hard drive removable media, RAM, or network buffer). The program 334 may include one or more sequences of executable code or coded instructions that are executed by the CPU 320. The program 334 may be loaded into the memory 332 from the storage device 336 or network or removable media. The CPU 320 may execute one or more sequences of instructions of the program 334 to process data. The program 334 may provide functionality as discussed herein.

The image and user-defined data may be entered via the data input device 338 or another input device, or received via the network 344 or other network. The data processor 310 may receive and store image and user-defined data in the memory 332, the storage device 336, or other storage unit. The program 334 may direct that the data received be stored on or read from machine-readable medium, including secondary storage devices such as hard disks, floppy disks, CD-ROMS, and DVDs; electromagnetic signals; or other forms of machine readable medium, either currently known or later developed.

The program 334 may instruct the data processor 310 to depict the original or modified images and/or other patient related information in one or more windows on the display 340, the external output device 342, or other display screen. The information presented may be depicted visually or textually. The data processor 310 may retrieve the image and/or user-defined data from machine-readable medium, including secondary storage devices such as hard disks, floppy disks, CD-ROMS, and DVDs; electromagnetic signals; or other forms of machine readable medium, either currently known or later developed.

The program 334 may direct the data processor 310 to scroll through a visual or textual depiction of the original or modified images and/or other patient related information. The data processor 310 may divide the display 340, output device 342, or other display screen into multiple virtual sub-regions. Each of the virtual sub-regions may be associated with a specific image and/or other patient information. For instance, the display may be split into four quadrants. Other sub-regions may be provided.

The data processor 310 may cause display of images and/or other patient related information on the display 340, output device 342, or other display screen. The image and user-defined data may correspond to anatomical structures and medical conditions to be analyzed. The data processor 310 also may display icons on the display 340, output device 342, or other display screen. The display 340, output device 342, or other display screen may be a touch screen, a touch pad, a haptic device, or other vibrational or physical feedback device.

Figure 4:
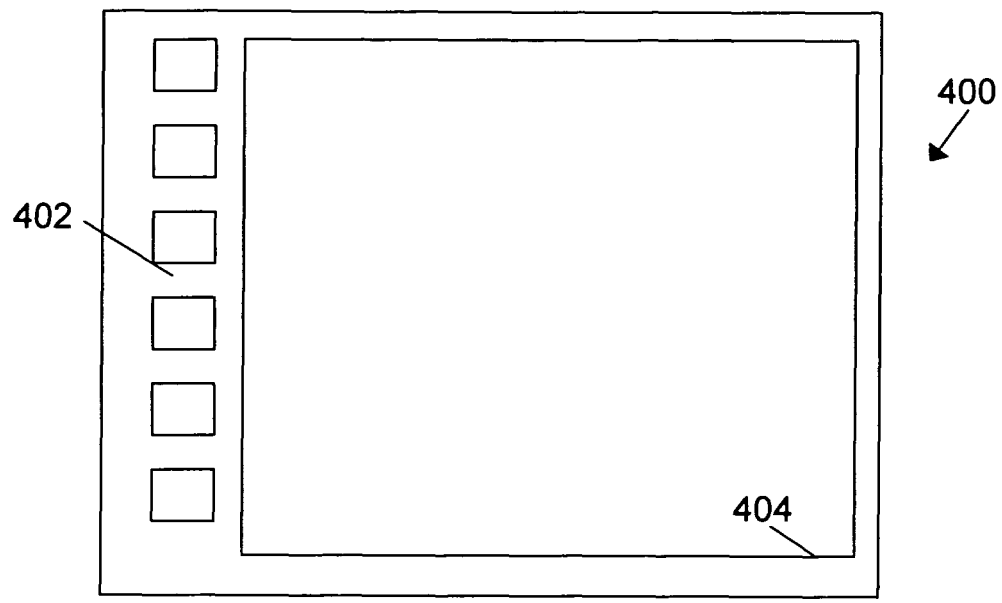
FIGS. 4 and 5 illustrate exemplary dedicated user interfaces operable to mark-up image data for simulation generation.

The user interface may accept one or more operations performed on the display and/or icons to reveal further information. For instance, the user interface may provide for the selection and display of a dedicated step page after the user clicks upon a step related icon. The dedicated step page may present further textual or graphical information related to a step in the workflow. The user interface also may present further textual or graphical information related to a specific patient or workflow step after user selection. Other operations may be performed FIG. 4 illustrates an exemplary dedicated user interface for marking up image data. The dedicated interface may be employed at both the remote medical facility and the service provider. As shown, the dedicated interface 400 may include one or more icons 402 and a primary window 404. The user interface 400 may include additional, fewer, or alternate components. In alternative embodiments, different user interfaces are provided at the medical facility and the service provider, but the interfaces are operable with the same data.

Each icon 402 may be associated with a different function. For instance, an icon may be related to a step in the workflow, a user-selected parameter or operation, patient information, various imaging procedures, a specific modified geometry, and/or other functions.

The primary window 404 may display images, as well as modified images or other information, as discussed herein. An operation performed on an icon 402, such as by a mouse, touch screen, or other input device, may result in the images and/or data displayed in the window 404 being changed to those associated with that icon 402. The icon 402 may be associated with rotation of or virtual flight thru the images.

Figure 5:
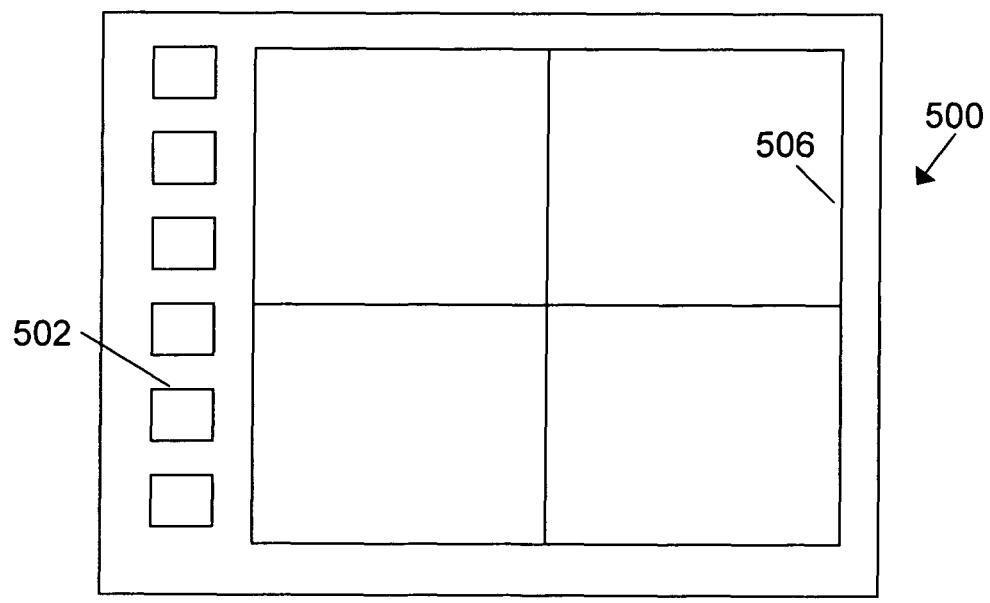

FIG. 5 illustrates another exemplary dedicated user interface for customizing image data for simulation generation. The user interface 500 may include a number of icons 502 and windows 506. The user interface 500 may include additional, fewer, or alternate components.

Each icon 502 may be associated with a different simulation or geometry generation related function. Each window 506 may display the simulation and interpretation results discussed herein, including images and geometries as modified by a user. An operation performed on an icon 502 may result in the images and/or data displayed in all or some of the windows 506 being changed to those associated with that icon 502.

The exemplary user interfaces of FIGS. 4 and 5 may provide functionality for rotating and/or translating along one or more axes of the two or three dimensional internal images acquired via various medical imaging procedures as discussed herein. The exemplary user interfaces may permit various images to be superimposed over one another to emphasize additional features, changes to the images, or other differences.

While the invention has been described above by reference to various embodiments, it should be understood that many changes and modifications can be made without departing from the scope of the invention. The description and illustrations are by way of example only. Many more embodiments and implementations are possible within the scope of this invention and will be apparent to those of ordinary skill in the art. The various embodiments are not limited to the described environments and have a wide variety of applications.

It is intended in the appended claims to cover all such changes and modifications which fall within the true spirit and scope of the invention. Therefore, the invention is not limited to the specific details, representative embodiments, and illustrated examples in this description. Accordingly, the invention is not to be restricted except in light as necessitated by the accompanying claims and their equivalents.

What is claimed is:

1. A method of medical diagnosis, the method comprising:
receiving data associated with a patient from a remote location via a communications network at a central location, the data including image data, segmentation data, and ancillary data;
generating, at the central location, a medical simulation for the patient based upon the data received from the remote location, the medical simulation including use of the ancillary data, the medical simulation being a representation over time of at least a part of the patient changing;
performing, at the central location, a medical diagnosis based on the generated medical simulation; and
transmitting the generated medical simulation and the medical diagnosis from the central location to the remote location via the communications network.

2. The method of claim 1, wherein generating the medical simulation comprises generating the medical simulation of a flow of blood within the patient using computational fluid dynamics algorithms.

3. The method of claim 1, wherein receiving the data associated with the patient comprises receiving the image data in a predetermined format.

4. The method of claim 1, wherein receiving the data associated with the patient comprises receiving the ancillary data including a simulation parameter associated with the patient.

5. The method of claim 4, wherein the simulation parameter relates to the viscosity of the patient's blood.

6. The method of claim 1, wherein receiving the data associated with the patient from the remote location comprises receiving the image data including a simulation-related recommendation associated with the patient that enhances the accuracy of the medical simulation.

7. The method of claim 6, wherein the recommendation includes a suggested modification of a segmented geometry.

8. The method of claim 6, wherein the recommendation includes defining the location or configuration of a vessel inlet or outlet.

9. The method of claim 6, wherein the recommendation includes a region of interest or artifact to analyze via the medical simulation.

10. The method of claim 1, wherein the image data is at least one of magnetic resonance, computed tomography, and angiography image data.

11. A method of image visualization for medical diagnosis, the method comprising:
receiving data associated with a patient from a remote location via a network at a central location;
performing a medical simulation at the central location, the medical simulation visually simulating blood flow over time within the patient based upon the data received from the remote location;
interpreting the medical simulation at the central location to produce a medical diagnosis; and
transmitting the medical diagnosis and data by which to visualize the medical simulation from the central location to the remote location via the network.

12. The method of claim 11, wherein the data includes image data acquired via at least one of a magnetic resonance procedure, a computer tomography procedure, and an angiography procedure.

13. The method of claim 11, wherein receiving the data associated with the patient from the remote location comprises receiving image data, a simulation parameter and a recommendation to enhance the accuracy of the medical simulation, and wherein performing the medical simulation comprises performing the medical simulation based upon the image data, the simulation parameter, and the recommendation received from the remote location.

14. The method of claim 13, wherein the simulation parameter relates to the viscosity of the patient's blood.

15. The method of claim 13, wherein the recommendation includes a suggested modification of a segmented geometry.

16. The method of claim 13, wherein the recommendation includes defining a vessel inlet or outlet.

17. The method of claim 13, wherein the recommendation includes at least one of a region of interest and an artifact to analyze via the medical simulation.

18. A data processing system for image visualization that facilitates medical diagnosis, the system comprising:
a memory unit operable to store image data associated with internal images of a patient;
a processing unit operable to access the image data stored and display a segmented geometry of an anatomical structure shown in the internal images on a display;
a user interface operable to accept a user-selected parameter associated with a modification of the segmented geometry to generate user-defined data, wherein the user-defined data is stored in the memory unit such that the modified segmented geometry is subsequently reconstructable using the user-defined data, the anatomical structure being a blood vessel and a first user-selected parameter defining an inlet or an outlet of the blood vessel;
an interface to a communications network, the interface configured to communicate with a central site and to receive data from the central site, the received data being simulation data based on the segmented geometry and the user-defined data, and medical diagnosis data based on the simulation data, the simulation data being a representation over time of at least a part of the patient changing; and
a display configured for visualizing the segmented data in combination with the simulation data received from the central cite.

19. The data processing system of claim 18, wherein a second user-selected parameter defines the viscosity of the patient's blood.

20. The data processing system of claim 18, wherein a third user-selected parameter relates to the patient's blood flow or pressure.

21. The data processing system of claim 18, wherein the system is operable to transfer the user-defined data via a network to a service provider and subsequently receive simulation data via the network from the service provider, and
wherein the processor is operable to reconstruct the simulation data to generate a medical simulation via the user interface, the medical simulation being based upon the user-defined data.

22. The data processing system of claim 18, wherein the system is operable to transfer the user-defined data via a network to a central processing unit and subsequently receive simulation data via the network from the central processing unit, and wherein the processor is operable to reconstruct the simulation data to generate a medical simulation via the user interface, the medical simulation being based upon the user-defined data.

23. The data processing system of claim 18, wherein the image data is magnetic resonance or computed tomography related data.

24. A non-transitory computer-readable medium having instructions executable on a computer, the instructions comprising:

receiving image data associated with internal images of a patient;

displaying a segmented geometry of an anatomical structure shown within the internal images;

accepting a user-selected operation that modifies the segmented geometry;

generating user-defined data that correlates the user-selected operation with the segmented geometry such that the segmented geometry as modified is subsequently reconstructable;

transferring the user-defined data via a network to a service provider; and receiving, from the service provider, simulation data generated at the service provider based on the modified segmented geometry, and medical diagnosis data generated at the service provider based on the simulation data, the simulation data being a representation over time of at least a part of the patient changing.

25. The non-transitory computer-readable medium of claim 24, the instructions comprising:

subsequently receiving simulation data from the service provider via the network; and reconstructing a medical simulation using the simulation data, where the medical simulation accounts for the user-selected operation.

26. The non-transitory computer-readable medium of claim 25, wherein the medical simulation simulates blood flow within the anatomical structure.

27. The non-transitory computer-readable medium of claim 25, wherein the instructions comprise searching a database based upon a patient characteristic to locate data associated with a previous patient having similar characteristics.

28. The method of claim 1, wherein receiving the data associated with the patient from the remote location comprises receiving the image data including a segmented representation of image data obtained at the remote location.

29. The method of claim 1, further comprising outputting data based on running the generated medical simulation, the output data representing the part of the patient changing such that at least a portion of the output data is different than at least a portion of the received data.

* * * * *